United States Patent [19]

Piper

[11] Patent Number: 5,689,036
[45] Date of Patent: Nov. 18, 1997

[54] HYBRID MAIZE PLANT AND SEED (3730)

[75] Inventor: Todd Elliott Piper, Eau Claire, Wis.

[73] Assignee: Pioneer Hi-Bred International, Inc., Des Moines, Iowa

[21] Appl. No.: 610,905

[22] Filed: Mar. 5, 1996

Related U.S. Application Data

[63] Continuation of Ser. No. 398,481, Mar. 3, 1995, abandoned.

[51] Int. Cl.$^6$ ............................. A01H 5/00; A01H 4/00; C12N 5/04
[52] U.S. Cl. ................. 800/200; 800/250; 800/DIG. 56; 435/412; 435/424; 435/430; 435/430.1; 47/58; 47/DIG. 1
[58] Field of Search ...................... 800/200, 205, 800/DIG. 56; 435/172.1, 240.4, 240.45, 240.49, 240.5, 412, 424, 430; 47/58, DIG. 1

[56] References Cited

U.S. PATENT DOCUMENTS 4,812,599   3/1989   Segebart.

FOREIGN PATENT DOCUMENTS 160390   11/1985   European Pat. Off..

OTHER PUBLICATIONS

Conger, B.V., et al. (1987) "Somatic Embryogenesis From Cultured Leaf Segments of *Zea Mays*", *Plant Cell Reports*, 6:345–347.

Duncan, D.R., et al. (1985) "The Production of Callus Capable of Plant Regeneration From Immature Embryos of Numerour *Zea Mays* Genotypes", *Planta*, 165:322–332.

Edallo, et al. (1981) "Chromosomal Variation and Frequency of Spontaneous Mutation Associated with in Vitro Culture and Plant Regeneration in Maize", *Maydica*, XXVI:39–56.

Green, et al., (1975) "Plant Regeneration From Tissue Cultures of Maize", *Crop Science*, vol. 15, pp. 417–421.

Green, C.E., et al. (1982) "Plant Regeneration in Tissue Cultures of Maize" *Maize for Biological Research*, pp. 367–372.

Hallauer, A.R. et al. (1988) "Corn Breeding" *Corn and Corn Improvement*, No. 18, pp. 463–481.

Meghji, M.R., et al. (1984). "Inbreeding Depression, Inbred & Hybrid Grain Yields, and Other Traits of Maize Genotypes Representing Three Eras", *Crop Science*, vol. 24, pp. 545–549.

Phillips, et al. (1988) "Cell/Tissue Culture and In Vitro Manipulation", *Corn & Corn Improvement*, 3rd Ed., ASA Publication, No. 18, pp. 345–387.

Poehlman (1987) *Breeding Field Crop*, AVI Publication Co., Westport, Ct., pp. 237–246.

Rao, K.V., et al., (1986) "Somatic Embryogenesis in Glume Callus Cultures", *Maize Genetics Cooperative Newsletter*, No. 60, pp. 64–65.

Sass, John F. (1977) "Morphology", *Corn & Corn Improvement*, ASA Publication. Madison, Wisconsin, pp. 89–109.

Songstad, D.D. et al. (1988) "Effect of ACC (1–aminocyclopropane–1–carboxylic acid), Silver Nitrate & Norbonadiene on Plant Regeneration From Maize Callus Cultures", *Plant Cell Reports*, 7:262–265.

Tomes, et al. (1985) "The Effect of Parental Genotype on Initiation of Embryogenic Callus From Elite Maize (*Zea Mays* L.) Germplasm", *Theor. Appl. Genet.*, vol. 70, pp. 505–509.

Troyer, et al. (1985) "Selection for Early Flowering in Corn: 10 Late Synthetics", *Crop Science*, vol. 25, pp. 695–697.

Umbeck, et al. (1983) "Reversion of Male–Sterile T–Cytoplasm Maize to Male Fertility in Tissue Culture", *Crop Science*, vol. 23, pp. 584–588.

Wright, Harold (1980) "Commercial Hybrid Seed Production", *Hybridization of Crop Plants*, Ch. 8: 161–176.

Wych, Robert D. (1988) "Production of Hybrid Seed", *Corn and Corn Improvement*, Ch. 9, pp. 565–607.

*Primary Examiner*—Gary Benzion
*Attorney, Agent, or Firm*—Pioneer Hi-Bred International, Inc.

[57] ABSTRACT

According to the invention, there is provided a hybrid maize plant, designated as 3730, produced by crossing two Pioneer Hi-Bred International, Inc. proprietary inbred maize lines. This invention relates to the hybrid seed 3730, the hybrid plant produced from the seed, and variants, mutants, and trivial modifications of hybrid 3730.

6 Claims, No Drawings

HYBRID MAIZE PLANT AND SEED (3730)

CROSS REFERENCE TO RELATED APPLICATION

This is a continuation of application Ser. No. 08/398,481, filed Mar. 3, 1995, now abandoned.

FIELD OF THE INVENTION

This invention is in the field of maize breeding, specifically relating to a hybrid maize line designated 3730.

BACKGROUND OF THE INVENTION

Plant Breeding

Field crops are bred through techniques that take advantage of the plant's method of pollination. A plant is self-pollinated if pollen from one flower is transferred to the same or another flower of the same plant. A plant is cross-pollinated if the pollen comes from a flower on a different plant.

Plants that have been self-pollinated and selected for type for many generations become homozygous at almost all gene loci and produce a uniform population of true breeding progeny. A cross between two different homozygous lines produces a uniform population of hybrid plants that may be heterozygous for many gene loci. A cross of two plants each heterozygous at a number of gene loci will produce a population of hybrid plants that differ genetically and will not be uniform.

Maize (Zea mays L.), often referred to as corn in the United States, can be bred by both self-pollination and cross-pollination techniques. Maize has separate male and female flowers on the same plant, located on the tassel and the ear, respectively. Natural pollination occurs in maize when wind blows pollen from the tassels to the silks that protrude from the tops of the ears.

The development of a hybrid maize variety involves three steps: (1) the selection of plants from various germplasm pools for initial breeding crosses; (2) the selfing of the selected plants from the breeding crosses for several generations to produce a series of inbred lines, which, although different from each other, breed true and are highly uniform; and (3) crossing the selected inbred lines with unrelated inbred lines to produce the hybrid progeny ($F_1$). During the inbreeding process in maize, the vigor of the lines decreases. Vigor is restored when two different inbred lines are crossed to produce the hybrid progeny ($F_1$). An important consequence of the homozygosity and homogeneity of the inbred lines is that the hybrid created by crossing a defined pair of inbreds will always be the same. Once the inbreds that create a superior hybrid have been identified, a continual supply of the hybrid seed can be produced using these inbred parents and the hybrid corn plants can then be generated from this hybrid seed supply.

Large scale commercial maize hybrid production, as it is practiced today, requires the use of some form of male sterility system which controls or inactivates male fertility. A reliable method of controlling male fertility in plants also offers the opportunity for improved plant breeding. This is especially true for development of maize hybrids, which relies upon some sort of male sterility system. There are several options for controlling male fertility available to breeders, such as: manual or mechanical emasculation (or detasseling), cytoplasmic male sterility, genetic male sterility, gametocides and the like.

Hybrid maize seed is typically produced by a male sterility system incorporating manual or mechanical detasseling. Alternate strips of two inbred varieties of maize are planted in a field, and the pollen-bearing tassels are removed from one of the inbreds (female). Providing that there is sufficient isolation from sources of foreign maize pollen, the ears of the detasseled inbred will be fertilized only from the other inbred (male), and the resulting seed is therefore hybrid and will form hybrid plants.

The laborious, and occasionally unreliable, detasseling process can be avoided by using cytoplasmic male-sterile (CMS) inbreds. Plants of a CMS inbred are male sterile as a result of factors resulting from the cytoplasmic, as opposed to the nuclear, genome. Thus, this characteristic is inherited exclusively through the female parent in maize plants, since only the female provides cytoplasm to the fertilized seed. CMS plants are fertilized with pollen from another inbred that is not male-sterile. Pollen from the second inbred may or may not contribute genes that make the hybrid plants male-fertile. Usually seed from detasseled fertile maize and CMS produced seed of the same hybrid are blended to insure that adequate pollen loads are available for fertilization when the hybrid plants are grown.

There are several methods of conferring genetic male sterility available, such as multiple mutant genes at separate locations within the genome that confer male sterility, as disclosed in U.S. Pat. Nos. 4,654,465 and 4,727,219 to Brat et al. and chromosomal translocations as described by Patterson in U.S. Pat. Nos. 3,861,709 and 3,710,511. These and all patents referred to are incorporated by reference. In addition to these methods, Albertsen et al., of Pioneer Hi-Bred, U.S. patent application Ser. No. 07/848,433, have developed a system of nuclear male sterility which includes: identifying a gene which is critical to male fertility; silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing, or turning "on", the promoter, which in turn allows the gene that confers male fertility to be transcribed.

There are many other methods of conferring genetic male sterility in the art, each with its own benefits and drawbacks. These methods use a variety of approaches such as delivering into the plant a gene encoding a cytotoxic substance associated with a male tissue specific promoter or an antisense system in which a gene critical to fertility is identified and an antisense to that gene is inserted in the plant (see: Fabinjanski, et al. EPO 89/3010153.8 publication no. 329, 308 and PCT application PCT/CA90/00037 published as WO 90/08828).

Another system useful in controlling male sterility makes use of gametocides. Gametocides are not a genetic system, but rather a topical application of chemicals. These chemicals affect cells that are critical to male fertility. The application of these chemicals affects fertility in the plants only for the growing season in which the gametocide is applied (see Carlson, Glenn R., U.S. Pat. No. 4,936,904). Application of the gametocide, timing of the application and genotype specificity often limit the usefulness of the approach.

The use of male sterile inbreds is but one factor in the production of maize hybrids. The development of maize hybrids requires, in general, the development of homozygous inbred lines, the crossing of these lines, and the evaluation of the crosses. Breeding programs combine the genetic backgrounds from two or more inbred lines or various other broad-based sources into breeding pools from which new inbred lines are developed by selfing and selection of desired phenotypes. The new inbreds are crossed with other inbred lines and the hybrids from these crosses are evaluated to determine which of those have commercial potential.

There are many important factors to be considered in the art of plant breeding, such as the ability to recognize important morphological and physiological characteristics, the ability to design evaluation techniques for genotypic and phenotypic traits of interest, and the ability to search out and exploit the genes for the desired traits in new or improved combinations.

The objective of commercial maize hybrid line development programs is to develop new inbred lines to produce hybrids that combine to produce high grain yields and superior agronomic performance. The primary trait breeders seek is yield. However, many other major agronomic traits are of importance in hybrid combination and have an impact on yield or otherwise provide superior performance in hybrid combinations. Such traits include percent grain moisture at harvest, relative maturity, resistance to stalk breakage, resistance to root lodging, grain quality, and disease and insect resistance. In addition, the lines per se must have acceptable performance for parental traits such as seed yields, kernel sizes, pollen production, all of which affect ability to provide parental lines in sufficient quantity and quality for hybridization. These traits have been shown to be under genetic control and many if not all of the traits are affected by multiple genes.

Pedigree Breeding

The pedigree method of breeding is the mostly widely used methodology for new hybrid line development.

In general terms this procedure consists of crossing two inbred lines to produce the non-segregating $F_1$ generation, and self pollination of the $F_1$ generation to produce the $F_2$ generation that segregates for all factors for which the inbred parents differ. An example of this process is set forth below. Variations of this generalized pedigree method are used, but all these variations produce a segregating generation which contains a range of variation for the traits of interest.

EXAMPLE 1

Hypothetical Example of Pedigree Breeding Program

Consider a cross between two inbred lines that differ for alleles at five loci. The parental genotypes are:

Parent 1 A b C d e F/A b C d e F

Parent 2 a B c D E f/a B c D E f the $F_1$ from a cross between these two parents is:

$F_1$ A b C d e F/a B c D E f

Selfing $F_1$ will produce an $F_2$ generation including the following genotypes:

A B c D E f/a b C d e F
A B c D e f/a b C d E F
A B c D e f/a b C d e F

The number of genotypes in the $F_2$ is $3^6$ for six segregating loci (729) and will produce $(2^6)-2$ possible new inbreds, (62 for six segregating loci).

Each inbred parent which is used in breeding crosses represents a unique combination of genes, and the combined effects of the genes define the performance of the inbred and its performance in hybrid combination. There is published evidence (Smith, O. S., J. S. C. Smith, S. L. Bowen, R,.A. Tenborg and S. J. Wall, TAG 80:833–840 (1990)) that each of the lines are different and can be uniquely identified on the basis of genetically-controlled molecular markers.

It has been shown (Hallauer, Arnel R. and Miranda, J. B. Fo. Quantitative *Genetics in Maize Breeding*, Iowa State University Press, Ames Iowa, 1981) that most traits of economic value in maize are under the genetic control of multiple genetic loci, and that there are a large number of unique combinations of these genes present in elite maize germplasm. If not, genetic progress using elite inbred lines would no longer be possible. Studies by Duvick and Russell (Duvick, D. N., *Maydica* 37:69–79, (1992); Russell, W. A., *Maydica* XXIX:375–390 (1983)) have shown that over the last 50 years the rate of genetic progress in commercial hybrids has been between one and two percent per year.

The number of genes affecting the trait of primary economic importance in maize, grain yield, has been estimated to be in the range of 10–1000. Inbred lines which are used as parents for breeding crosses differ in the number and combination of these genes. These factors make the plant breeders task more difficult. Compounding this is evidence that no one line contains the favorable allele at all loci, and that different alleles have different economic values depending on the genetic background and field environment in which the hybrid is grown. Fifty years of breeding experience suggests that there are many genes affecting grain yield and each of these has a relatively small effect on this trait. The effects are small compared to breeders ability to measure grain yield differences in evaluation trials. Therefore, the parents of the breeding cross must differ at several of these loci so that the genetic differences in the progeny will be large enough that breeders can develop a line that increases the economic worth of its hybrids over that of hybrids made with either parent.

If the number of loci segregating in a cross between two inbred lines is n, the number of unique genotypes in the $F_2$ generation is $3^n$ and the number of unique inbred lines from this cross is $\{(2^n)-2\}$. Only a very limited number of these combinations are useful. Only about 1 in 10,000 of the progeny from $F_2$'s are commercially useful.

By way of example, if it is assumed that the number of segregating loci in $F_2$ is somewhere between 20 and 50, and that each parent is fixed for half the favorable alleles, it is then possible to calculate the approximate probabilities of finding an inbred that has the favorable allele at $\{(n/2)+m\}$ loci, where n/2 is the number of favorable alleles in each of the parents and m is the number of additional favorable alleles in the new inbred. See Example 2 below. The number m is assumed to be greater than three because each allele has so small an effect that evaluation techniques are not sensitive enough to detect differences due to three or less favorable alleles. The probabilities in Example 2 are on the order of $10^{-5}$ or smaller and they are the probabilities that at least one genotype with (n/2)=m favorable alleles will exist.

To put this in perspective, the number of plants grown on 60 million acres (approximate United States corn acreage) at 25,000 plants/acre is $1.5 \times 10^{12}$.

EXAMPLE 2

Probability of Finding an Inbred with m of n Favorable Alleles

Assume each parent has n/2 of the favorable alleles and only ½ of the combinations of loci are economically useful.

| No. of segregating loci (n) | No. of favorable alleles in Parents (n/2) | No. additional favorable alleles in new inbred | Probability that genotype occurs* |
| --- | --- | --- | --- |
| 20 | 10 | 14 | $3 \times 10^{-5}$ |
| 24 | 12 | 16 | $2 \times 10^{-5}$ |
| 28 | 14 | 18 | $1 \times 10^{-6}$ |
| 32 | 16 | 20 | $8 \times 10^{-6}$ |
| 36 | 18 | 22 | $5 \times 10^{-6}$ |
| 40 | 20 | 24 | $3 \times 10^{-6}$ |
| 44 | 22 | 26 | $2 \times 10^{-6}$ |
| 48 | 24 | 28 | $1 \times 10^{-6}$ |

*Probability that a useful combination exists, does not include the probability of identifying this combination if it does exist.

The possibility of having a usably high probability of being able to identify this genotype based on replicated field testing would be most likely smaller than this, and is a function of how large a population of genotypes is tested and how testing resources are allocated in the testing program.

Pioneer research station staff propose about 400 to 500 new inbreds each year from over 2,000,000 pollinations. Of those proposed new inbreds, less than 50, and more commonly less than 30, are actually selected for commercial use.

SUMMARY OF THE INVENTION

According to the invention, there is provided a hybrid maize plant, designated as 3730, produced by crossing two Pioneer Hi-Bred International, Inc proprietary inbred maize lines. This invention thus relates to the hybrid seed 3730, the hybrid plant produced from the seed, and variants, mutants, and trivial modifications of hybrid 3730. This hybrid maize plant is characterized by high yield, strong stalks, excellent early season growth and rapid dry-down after reaching maturity. It is best adapted for the North Central Region of the United States.

DEFINITIONS

In the description and examples that follow, a number of terms are used herein. In order to provide a clear and consistent understanding of the specification and claims, including the scope to be given such terms, the following definitions are provided. NOTE: ABS is in absolute terms and %MN is percent of the mean for the experiments in which the inbred or hybrid was grown. These designators will follow the descriptors to denote how the values are to be interpreted. Below are the descriptors used in the data tables included herein.

ANT ROT=ANTHRACNOSE STALK ROT (*Colletotrichum graminicola*), A 1 to 9 visual rating indicating the resistance to Anthracnose Stalk Rot. A higher score indicates a higher resistance.

BAR PLT=BARREN PLANTS. The percent of plants per plot that were not barren (lack ears).

BRT STK=BRITTLE STALKS. This is a measure of the stalk breakage near the time of pollination, and is an indication of whether a hybrid or inbred would snap or break near the time of flowering under severe winds. Data are presented as percentage of plants that did not snap in paired comparisons and on a 1 to 9 scale (9=highest resistance) in Characteristics Charts.

BU ACR=YIELD (BUSHELS/ACRE). Yield of the grain at harvest in bushels per acre adjusted to 15.5% moisture.

CLN=CORN LETHAL NECROSIS (synergistic interaction of maize chlorotic mottle virus (MCMV) in combination with either maize dwarf mosaic virus (MDMV-A or MDMV-B) or wheat streak mosaic virus (WSMV)). A 1 to 9 visual rating indicating the resistance to Corn Lethal Necrosis. A higher score indicates a higher resistance.

COM RST=COMMON RUST (*Puccinia sorghum*). A 1 to 9 visual rating indicating the resistance to Common Rust. A higher score indicates a higher resistance.

CRM=COMPARATIVE RELATIVE MATURITY (see PRM).

D/D=DRYDOWN. This represents the relative rate at which a hybrid will reach acceptable harvest moisture compared to other hybrids on a 1–9 rating scale. A high score indicates a hybrid that dries relatively fast while a low score indicates a hybrid that dries slowly.

D/E=DROPPED EARS. Represented in a 1 to 9 scale in the Characteristics Chart, where 9 is the rating representing the least, or no, dropped ears.

DIP ERS=DIPLODIA EAR MOLD SCORES (*Diplodia maydis* and *Diplodia macrospora*). A 1 to 9 visual rating indicating the resistance to Diplodia Ear Mold. A higher score indicates a higher resistance.

DRP EAR=DROPPED EARS. A measure of the number of dropped ears per plot and represents the percentage of plants that did not drop ears prior to harvest.

D/T=DROUGHT TOLERANCE. This represents a 1–9 rating for drought tolerance, and is based on data obtained under stress conditions. A high score indicates good drought tolerance and a low score indicates poor drought tolerance.

EAR HT=EAR HEIGHT. The ear height is a measure from the ground to the highest placed developed ear node attachment and is measured in inches. This is represented in a 1 to 9 scale in the Characteristics Chart, where 9 is highest.

EAR MLD=General Ear Mold. Visual rating (1–9 score) where a "1" is very susceptible and a "9" is very resistant. This is based on overall rating for ear mold of mature ears without determining the specific mold organism, and may not be predictive for a specific ear mold.

EAR SZ=EAR SIZE. A 1 to 9 visual rating of ear size. The higher the rating the larger the ear size.

ECB 1LF=EUROPEAN CORN BORER FIRST GENERATION LEAF FEEDING (*Ostrinia nubilalis*). A 1 to 9 visual rating indicating the resistance to preflowering leaf feeding by first generation European Corn Borer. A higher score indicates a higher resistance.

ECB 2IT=EUROPEAN CORN BORER SECOND GENERATION INCHES OF TUNNELING (*Ostrinia nubilalis*). Average inches of tunneling per plant in the stalk.

ECB 2SC=EUROPEAN CORN BORER SECOND GENERATION (*Ostrinia nubilalis*). A 1 to 9 visual rating indicating post flowering degree of stalk breakage and other evidence of feeding by European Corn Borer, Second Generation. A higher score indicates a higher resistance.

ECB DPE=EUROPEAN CORN BORER DROPPED EARS (*Ostrinia nubilalis*). Dropped ears due to European Corn Borer. Percentage of plants that did not drop ears under second generation corn borer infestation.

E/G=EARLY GROWTH. This represents a 1 to 9 rating for early growth, scored when two leaf collars are visible.

EST CNT=EARLY STAND COUNT. This is a measure of the stand establishment in the spring and represents the number of plants that emerge on per plot basis for the inbred or hybrid.

EYE SPT=Eye Spot (*Kabatiella zeae* or *Aureobasidium zeae*). A 1 to 9 visual rating indicating the resistance to Eye Spot. A higher score indicates a higher resistance.

FUS ERS=FUSARIUM EAR ROT SCORE (*Fusarium moniliforme* or *Fusarium subglutinans*). A 1 to 9 visual rating indicating the resistance to Fusarium ear rot. A higher score indicates a higher resistance.

G/A=GRAIN APPEARANCE. Appearance of grain in the grain tank (scored down for mold, cracks, read streak, etc.).

GDU=Growing Degree Units. Using the Barger Heat Unit Theory, that assumes that maize growth occurs in the temperature range 50° F.–86° F. and that temperatures outside this range slow down growth; the maximum daily heat unit accumulation is 36 and the minimum daily heat unit accumulation is 0. The seasonal accumulation of GDU is a major factor in determining maturity zones.

GDU PHY=GDU TO PHYSIOLOGICAL MATURITY. The number of growing degree units required for an inbred or hybrid line to have approximately 50 percent of plants at physiological maturity from time of planting. Growing degree units are calculated by the Barger method.

GDU SHD=GDU TO SHED. The number of growing degree units (GDUs) or heat units required for an inbred line or hybrid to have approximately 50 percent of the plants shedding pollen and is measured from the time of planting. Growing degree units are calculated by the Barger Method, where the heat units for a 24-hour period are:

$$GDU = \frac{(Max.\ temp.\ +\ Min.\ temp.)}{2} - 50$$

The highest maximum temperature used is 86° F. and the lowest minimum temperature used is 50° F. For each inbred or hybrid it takes a certain number of GDUs to reach various stages of plant development.

GDU SLK=GDU TO SILK. The number of growing degree units required for an inbred line or hybrid to have approximately 50 percent of the plants with silk emergence from time of planting. Growing degree units are calculated by the Barger Method as given in GDU SHD definition.

GIB ERS=GIBBERELLA EAR ROT (PINK MOLD) (*Gibberella zeae*). A 1 to 9 visual rating indicating the resistance to Gibberella Ear Rot. A higher score indicates a higher resistance.

GLF SPT=Gray Leaf Spot (*Cercospora zeae-maydis*). A 1 to 9 visual rating indicating the resistance to Gray Leaf Spot. A higher score indicates a higher resistance.

GOS WLT=Goss' Wilt (*Corynebacterium nebraskense*). A 1 to 9 visual rating indicating the resistance to Goss' Wilt. A higher score indicates a higher resistance.

GRN APP=GRAIN APPEARANCE. This is a 1 to 9 rating for the general appearance of the shelled grain as it is harvested based on such factors as the color of harvested grain, any mold on the grain, and any cracked grain. High scores indicate good grain quality.

H/POP=YIELD AT HIGH DENSITY. Yield ability at relatively high plant densities on 1–9 relative rating system with a higher number indicating the hybrid responds well to high plant densities for yield relative to other hybrids. A 1, 5, and 9 would represent very poor, average, and very good yield response, respectively, to increased plant density.

HC BLT=HELMINTHOSPORIUM CARBONUM LEAF BLIGHT (*Helminthosporium carbonum*). A 1 to 9 visual rating indicating the resistance to Helminthosporium infection. A higher score indicates a higher resistance.

HD SMT=HEAD SMUT (*Sphacelotheca reiliana*). This score indicates the percentage of plants not infected.

INC D/A=GROSS INCOME (DOLLARS PER ACRE). Relative income per acre assuming drying costs of two cents per point above 15.5 percent harvest moisture and current market price per bushel.

INCOME/ACRE. Income advantage of hybrid to be patented over other hybrid on per acre basis.

INC ADV=GROSS INCOME ADVANTAGE, GROSS INCOME advantage of variety #1 over variety #2.

L/POP=YIELD AT LOW DENSITY. Yield ability at relatively low plant densities on a 1–9 relative system with a higher number indicating the hybrid responds well to low plant densities for yield relative to other hybrids. A 1, 5, and 9 would represent very poor, average, and very good yield response, respectively, to low plant density.

MDM CPX=MAIZE DWARF MOSAIC COMPLEX (MDMV=Maize Dwarf Mosaic Virus and MCDV=Maize Chlorotic Dwarf Virus). A 1 to 9 visual rating indicating the resistance to Maize Dwarf Mosaic Complex. A higher score indicates a higher resistance.

MST=HARVEST MOISTURE. The moisture is the actual percentage moisture of the grain at harvest.

MST ADV=MOISTURE ADVANTAGE. The moisture advantage of variety #1 over variety #2 as calculated by: MOISTURE of variety #2—MOISTURE of variety #1=MOISTURE ADVANTAGE of variety #1.

NLF BLT=Northern Leaf Blight (*Helminthosporium turcicum* or *Exserohilum turcicum*). A 1 to 9 visual rating indicating the resistance to Northern Leaf Blight. A higher score indicates a higher resistance.

PHY CRM=CRM at physiological maturity.

PLT HT=PLANT HEIGHT. This is a measure of the height of the plant from the ground to the tip of the tassel in inches. This is represented as a 1 to 9 scale, 9 highest, in the Characteristics Chart.

POL SC=POLLEN SCORE. A 1 to 9 visual rating indicating the amount of pollen shed. The higher the score the more pollen shed.

POL WT=POLLEN WEIGHT. This is calculated by dry weight of tassels collected as shedding commences minus dry weight from similar tassels harvested after shedding is complete.

It should be understood that the inbred can, through routine manipulation of cytoplasmic or other factors, be produced in a male-sterile form. Such embodiments are also contemplated within the scope of the present claims.

POP K/A=PLANT POPULATIONS. Measured as 1000s per acre.

POP ADV=PLANT POPULATION ADVANTAGE. The plant population advantage of variety #1 over variety #2 as calculated by PLANT POPULATION of variety #2=PLANT POPULATION of variety #1=PLANT POPULATION ADVANTAGE of variety #1.

PRM=PREDICTED Relative Maturity. This trait, predicted relative maturity, is based on the harvest moisture of the grain. The relative maturity rating is based on a known set of checks and utilizes standard linear regression analyses and is referred to as the Comparative Relative Maturity Rating System that is similar to the Minnesota Relative Maturity Rating System.

PRM SHD=A relative measure of the growing degree units (GDU) required to reach 50% pollen shed. Relative values are predicted values from the linear regression of observed GDU's on relative maturity of commercial checks.

PRO=PROTEIN RATING. Rating on a 1 to 9 scale comparing relative amount of protein in the grain compared to hybrids of similar maturity. A "1" score difference represents a 0.4 point change in grain protein percent (e.g., 8.0% to 8.4%).

P/Y=PROTEIN/YIELD RATING. Indicates, on a 1 to 9 scale, the economic value of a hybrid for swine and poultry feeders. This takes into account the income due to yield, moisture and protein content.

ROOTS (%)=Percent of stalks NOT root lodged at harvest.

R/L=ROOT LODGING. A 1 to 9 rating indicating the level of root lodging resistance. The higher score represents higher levels of resistance.

RT LDG=ROOT LODGING. Root lodging is the percentage of plants that do not root lodge; plants that lean from the vertical axis as an approximately 30° angle or greater would be counted as root lodged.

RTL ADV=ROOT LODGING ADVANTAGE. The root lodging advantage of variety #1 over variety #2.

S/L=STALK LODGING. A 1 to 9 rating indicating the level of stalk lodging resistance. The higher scores represent higher levels of resistance.

SCT GRN=SCATTER GRAIN. A 1 to 9 visual rating indicating the amount of scatter grain (lack of pollination or kernel abortion) on the ear. The higher the score the less scatter grain.

SDG VGR=SEEDLING VIGOR. This is the visual rating (1 to 9) of the amount of vegetative growth after emergence at the seedling stage (approximately five leaves). A higher score indicates better vigor.

SEL IND=SELECTION INDEX. The selection index gives a single measure of the hybrid's worth based on information for up to five traits. A maize breeder may utilize his or her own set of traits for the selection index. One of the traits that is almost always included is yield. The selection index data presented in the tables represent the mean value averaged across testing stations.

SLF BLT=SOUTHERN LEAF BLIGHT (*Helminthosporium maydis* or *Bipolaris maydis*). A 1 to 9 visual rating indicating the resistance to Southern Leaf Blight. A higher score indicates a higher resistance.

SLK CRM=CRM at Silking.

SOU RST=SOUTHERN RUST (*Puccinia polysora*). A 1 to 9 visual rating indicating the resistance to Southern Rust, A higher score indicates a higher resistance.

STA GRN=STAYGREEN. Staygreen is the measure of plant health near the time of black layer formation (physiological maturity). A high score indicates better late-season plant health.

STAND (%)=Percent of stalks standing at harvest.

STD ADV=STALK STANDING ADVANTAGE. The advantage of variety #1 over variety #2 for the trait STK CNT.

STK CNT=NUMBER OF PLANTS. This is the final stand or number of plants per plot.

STK LDG=STALK LODGING. This is the percentage of plants that did not stalk lodge (stalk breakage) as measured by either natural lodging or pushing the stalks and determining the percentage of plants that break below the ear.

STW WLT=Stewart's Wilt (*Erwinia stewartii*). A 1 to 9 visual rating indicating the resistance to Stewart's Wilt. A higher score indicates a higher resistance.

TAS BLS=TASSEL BLAST. A 1 to 9 visual rating was used to measure the degree of blasting (necrosis due to heat stress) of the tassel at the time of flowering. A 1 would indicate a very high level of blasting at time of flowering, while a 9 would have no tassel blasting.

TAS SZ=TASSEL SIZE. A 1 to 9 visual rating was used to indicate the relative size of the tassel. The higher the rating the larger the tassel.

TAS WT=TASSEL WEIGHT. This is the average weight of a tassel (grams) just prior to pollen shed.

TEX EAR=EAR TEXTURE. A 1 to 9 visual rating was used to indicate the relative hardness (smoothness of crown) of mature grain. A 1 would be very soft (extreme dent) while a 9 would be very hard (flinty or very smooth crown).

TIL LER=TILLERS. A count of the number of tillers per plot that could possibly shed pollen was taken. Data is given as a percentage of tillers: number of tillers per plot divided by number of plants per plot.

TST WT (CHARACTERISTICS CHART)=Test weight on a 1 to 9 rating scale with a 9 being the highest rating.

TST WT=TEST WEIGHT (UNADJUSTED). The measure of the weight of the grain in pounds for a given volume (bushel).

TST WTA=TEST WEIGHT ADJUSTED. The measure of the weight of the grain in pounds for a given volume (bushel) adjusted for 15.5 percent moisture.

TSW ADV=TEST WEIGHT ADVANTAGE. The test weight advantage of variety #1 over variety #2.

WIN M %=PERCENT MOISTURE WINS.

WIN Y %=PERCENT YIELD WINS.

YLD=YIELD. It is the same as BU ACR ABS.

YLD ADV=YIELD ADVANTAGE. The yield advantage of variety #1 over variety #2 as calculated by: YIELD of variety #1=YIELD variety #2=yield advantage of variety #1.

YLD SC=YIELD SCORE. A 1 to 9 visual rating was used to give a relative rating for yield based on plot ear piles. The higher the rating the greater visual yield appearance.

DETAILED DESCRIPTION OF THE INVENTION

Pioneer Brand Hybrid 3730 is a single cross, yellow endosperm, dent maize hybrid with high yield in its maturity. Hybrid 3730 demonstrates an unexpected, excellent early season growth that is very rapid relative to other hybrids for its maturity. In addition, Hybrid 3730 has very good stalks and rapid dry-down after reaching maturity. Hybrid 3730 also demonstrates improved staygreen over other hybrids in its maturity.

This hybrid has the following characteristics based on the data collected primarily at Johnston, Iowa.

TABLE 1

VARIETY DESCRIPTION INFORMATION
HYBRID = PIONEER BRAND 3730

Type: Dent                              Region Best Adapted: North

A. Minnesota Relative Maturity Rating (harvest moisture): 101
   GDU's to Physiological Maturity (black layer): 2390
   GDU's to 50% Silk: 1230
B. Plant Characteristics:
   Plant height (to tassel tip): 297 cm
   Length of top ear internode: 19 cm
   Number of ears per stalk: Single
   Ear height (to base of top ear): 108 cm
   Number of tillers: None
   Cytoplasm type: Normal
C  Leaf:
   Color: (B14) Dark Green*
   Angle from Stalk: <25 degrees
   Marginal Waves: (OH7L) Many
   Number of Leaves (mature plants): 19
   Sheath Pubescence: (W22) Light
   Longitudinal Creases: (OH56A) Few

TABLE 1-continued

VARIETY DESCRIPTION INFORMATION
HYBRID = PIONEER BRAND 3730

Type: Dent      Region Best Adapted: North

Length (Ear node leaf): 93 cm
    Width (widest point, ear node leaf): 11 cm
D. Tassel:
    Number lateral branches: 5
    Branch Angle from central spike: 30–40 degrees
    Pollen Shed: (KY21) Heavy
    Peduncle Length (top leaf to basal branches): 19 cm
    Anther Color: Pink*
    Glume Color: Green*
E. Ear (Husked Ear Data Except When Stated Otherwise):
    Length: 18 cm
    Weight: 220 gm
    Mid-point Diameter: 47 mm
    Silk Color: Pink*
    Husk Extension (Harvest stage): Medium (Barely covering ear)
    Husk Leaf: Long(>15 cm)
    Taper of Ear: Average
    Position of Shank (dry husks): Upright
    Kernel Rows: Slightly curved, Distinct Number = 14
    Husk Color (fresh): Light Green*
    Husk Color (dry): Buff*
    Shank Length: 14 cm
    Shank (No. of internodes): 9
F. Kernel (Dried).
    Size (from ear mid-point)
    Length: 14 mm
    Width: 8 mm
    Thick: 4 mm
    Shape Grade (% rounds): 10
    Pericarp Color: Colorless*
    Aleurone Color: Homozygous Yellow*
    Endosperm Color: Yellow*
    Endosperm Type: Normal
    Gm Wt/100 Seeds (unsized): 33 gm
G. Cob:
    Diameter at mid-point: 24 mm
    Strength: Strong
    Color: Red*
H. Diseases:
    N. Leaf Blight (*E. turcicum*): Intermediate
    Eye Spot (*K. zeae*): Resistant
    Gray Leaf Spot (*C. zeae*): Susceptible
    Goss's Wilt (*C. nebraskense*): Resistant
    Fusarium Ear Mold (*F. moniliforme*): Resistant
    Gibberella Ear Rot (*G. zeae*): Intermediate
I. Insects:
    European Corn Borer-2 (Post-flowering): Intermediate
    The above descriptions are based on a scale of 1–9, 1 being highly susceptible 9 being highly resistant.
    S (Susceptible): Would generally represent a score of 1–3.
    I (Intermediate): Would generally represent a score of 4–5.
    R (Resistant): Would generally represent a score of 6–7.
    H (Highly Resistant): Would generally represent a score of 8–9.
    Highly resistant does not imply the inbred is immune.
J. Variety Most Closely Resembling:
    Character  Hybrid
    Maturity  Pioneer Brand 3733
    Usage  Pioneer Brand 3733

*In interpreting the foregoing color designations, reference may be had to the Munsell Glossy Book of Color, a standard color reference.

Data for Items B, C, D, E, F, and G is based primarily on a maximum of two reps from Johnston, Iowa grown in 1994.

Research Comparisons for Pioneer Hybrid 3730

Comparisons of characteristics for Pioneer Brand Hybrid 3730 were made against Pioneer Brand Hybrids 3723, 3733, 3714 and 3563. Table 2A compares Pioneer Brand Hybrid 3730 and Pioneer Brand Hybrid 3723. The results show Hybrid 3730 is significantly higher yielding than Hybrid 3723. In addition, Hybrid 3730 has a higher seedling vigor score and a higher early stand count than Hybrid 3723.

Table 2B compares Pioneer Hybrid 3730 and Pioneer Hybrid 3733. The results show Hybrid 3730 is significantly higher yielding than Hybrid 3733. In addition, Hybrid 3730 has a significantly higher seedling vigor score and a significantly higher resistance to stalk lodging than Hybrid 3733.

Table 2C compares Pioneer Hybrid 3730 and Pioneer Hybrid 3714. The results show the hybrids to have similar yields. Hybrid 3730 has taller plants than Hybrid 3714.

Table 2D compares Pioneer Hybrid 3730 and Pioneer Hybrid 3563. The results show Hybrid 3730 is higher yielding with higher seedling vigor than Hybrid 3563.

TABLE 2A

PAIRED COMPARISON REPORT
VARIETY #1 = 3730
VARIETY #2 = 3723
* = 10% SIG + = 5% SIG # = 1% SIG

| | VAR # | BU ACR ABS | BU ACR % MN | MST ABS | TST WT ABS | SDG VGR ABS | EST CNT ABS | TIL LER ABS | GDU SHD ABS |
|---|---|---|---|---|---|---|---|---|---|
| TOTAL SUM | 1 | 154.7 | 106 | 26.6 | 53.1 | 7.1 | 62.7 | 3.8 | 101.8 |
| | 2 | 143.6 | 97 | 25.6 | 52.9 | 5.0 | 59.6 | 2.9 | 102.8 |
| | LOCS | 55 | 55 | 56 | 42 | 36 | 31 | 5 | 18 |
| | REPS | 75 | 75 | 76 | 53 | 49 | 38 | 10 | 28 |
| | DIFF | 11.1 | 8 | 1.0 | 0.2 | 2.1 | 3.1 | 0.9 | 1.0 |
| | PROB | .000# | .000# | .000# | .329 | .000# | .006# | .375 | .127 |

| | VAR # | GDU SLK ABS | PLT HT ABS | EAR HT ABS | RT LDG ABS | STA GRN ABS | STK LDG ABS | BRT STK ABS | GRN APP ABS |
|---|---|---|---|---|---|---|---|---|---|
| TOTAL SUM | 1 | 115.0 | 108.5 | 45.2 | 94.5 | 5.3 | 96.8 | 98.0 | 6.4 |
| | 2 | 117.7 | 110.0 | 50.6 | 93.4 | 5.5 | 96.2 | 90.5 | 5.9 |
| | LOCS | 9 | 33 | 33 | 23 | 14 | 48 | 7 | 19 |

TABLE 2A-continued

PAIRED COMPARISON REPORT
VARIETY #1 = 3730
VARIETY #2 = 3723
* = 10% SIG + = 5% SIG # = 1% S1G

|  |  |  |  |  |  |  |  |  |  |
|---|---|---|---|---|---|---|---|---|---|
|  | REPS | 13 | 47 | 47 | 33 | 24 | 63 | 11 | 21 |
|  | DIFF | 2.7 | 1.6 | 5.3 | 1.1 | 0.3 | 0.6 | 7.5 | 0.5 |
|  | PROB | .006# | .044+ | .000# | .652 | .588 | .506 | .104 | .078* |

|  | VAR # | BAR PLT ABS | DRP EAR ABS | FUS ERS ABS | EYE SPT ABS | ECB DPE ABS | ECB 1LF ABS | ECB 2SC ABS |
|---|---|---|---|---|---|---|---|---|
| TOTAL SUM | 1 | 99.3 | 100.0 | 8.7 | 4.0 | 100.0 | 7.0 | 8.0 |
|  | 2 | 99.4 | 100.0 | 7.8 | 4.0 | 100.0 | 6.0 | 6.0 |
|  | LOCS | 3 | 26 | 3 | 1 | 3 | 1 | 1 |
|  | REPS | 6 | 30 | 6 | 1 | 3 | 1 | 2 |
|  | DIFF | 0.1 | 0.0 | 0.8 | 0.0 | 0.0 | 1.0 | 2.0 |
|  | PROB | .889 | 1.00 | .038+ |  | 1.00 |  |  |

TABLE 2B

PAIRED COMPARISON REPORT
VARIETY #1 = 3730
VARIETY #2 = 3723
* = 10% SIG + = 5% SIG # = 1% S1G

|  | VAR # | BU ACR ABS | BU ACR % MN | MST ABS | TST WT ABS | SDG VGR ABS | EST CNT ABS | TIL LER ABS | GDU SHD ABS |
|---|---|---|---|---|---|---|---|---|---|
| TOTAL SUM | 1 | 166.4 | 104 | 25.4 | 53.3 | 6.9 | 57.4 | 5.2 | 122.0 |
|  | 2 | 158.0 | 99 | 24.9 | 54.9 | 5.3 | 57.4 | 14.1 | 124.9 |
|  | LOCS | 252 | 252 | 259 | 176 | 105 | 162 | 5 | 96 |
|  | REPS | 327 | 327 | 334 | 212 | 148 | 210 | 8 | 121 |
|  | DIFF | 8.4 | 5 | 0.5 | 1.7 | 1.6 | 0.0 | 8.9 | 2.9 |
|  | PROB | .000# | .000# | .000# | .000# | .000# | .961 | .166 | .000# |

|  | VAR # | GDU SLK ABS | PLT HT ABS | EAR HT ABS | RT LDG ABS | STA GRN ABS | STK LDG ABS | BRT STK ABS | GRN APP ABS |
|---|---|---|---|---|---|---|---|---|---|
| TOTAL SUM | 1 | 121.1 | 108.7 | 43.5 | 91.1 | 4.8 | 97.2 | 96.8 | 6.3 |
|  | 2 | 124.9 | 106.9 | 45.7 | 92.8 | 5.0 | 90.2 | 99.3 | 6.7 |
|  | LOCS | 38 | 128 | 105 | 114 | 71 | 227 | 34 | 45 |
|  | REPS | 52 | 159 | 136 | 151 | 92 | 282 | 44 | 55 |
|  | DIFF | 3.8 | 1.8 | 2.3 | 1.8 | 0.2 | 7.0 | 2.5 | 0.4 |
|  | PROB | .000# | .000# | .000# | .110 | .265 | .000# | .024+ | .015+ |

|  | VAR # | EAR MLD ABS | BAR PLT ABS | DRP EAR ABS | GLF SPT ABS | NLF BLT ABS | GOS WLT ABS | HD SMT ABS | FUS ERS ABS |
|---|---|---|---|---|---|---|---|---|---|
| TOTAL SUM | 1 | 7.5 | 99.3 | 99.9 | 2.8 | 5.3 | 6.5 | 98.7 | 7.7 |
|  | 2 | 9.0 | 99.7 | 99.8 | 3.5 | 5.1 | 7.0 | 96.5 | 6.8 |
|  | LOCS | 1 | 3 | 169 | 3 | 13 | 2 | 5 | 6 |
|  | REPS | 2 | 6 | 197 | 5 | 23 | 4 | 9 | 12 |
|  | DIFF | 1.5 | 0.4 | 0.1 | 0.7 | 0.2 | 0.5 | 2.2 | 0.9 |
|  | PROB |  | .585 | .051* | .184 | .445 | .500 | .091* | .330 |

|  | VAR # | GIB ERS ABS | EYE SPT ABS | COM RST ABS | ECB DPE ABS | ECB 1LF ABS | ECB 2SC ABS | ECB 2IT ABS |
|---|---|---|---|---|---|---|---|---|
| TOTAL SUM | 1 | 5.6 | 6.3 | 5.5 | 99.1 | 5.2 | 5.2 | 3.8 |
|  | 2 | 7.2 | 5.5 | 6.5 | 99.1 | 6.1 | 5.4 | 3.7 |
|  | LOCS | 6 | 29 | 2 | 13 | 5 | 13 | 2 |
|  | REPS | 12 | 33 | 2 | 17 | 12 | 24 | 6 |
|  | DIFF | 1.6 | 0.7 | 1.0 | 0.0 | 0.8 | 0.2 | 0.0 |
|  | PROB | .115 | .008# | .000# | .969 | .049+ | .628 | .972 |

TABLE 2C

PAIRED COMPARISON REPORT
VARIETY #1 = 3730
VARIETY #2 = 3714
* = 10% SIG + = 5% SIG # = 1% SIG

| | VAR # | BU ACR ABS | BU ACR % MN | MST ABS | SDG VGR ABS | TIL LER ABS | GDU SHD ABS | PLT HT ABS |
|---|---|---|---|---|---|---|---|---|
| TOTAL | 1 | 159.0 | 102 | 17.1 | 8.0 | 4.6 | 77.5 | 112.1 |
| SUM | 2 | 161.1 | 104 | 18.3 | 7.0 | 0.3 | 78.3 | 109.9 |
| | LOCS | 3 | 3 | 3 | 3 | 3 | 3 | 8 |
| | REPS | 6 | 6 | 6 | 6 | 6 | 6 | 16 |
| | DIFF | 2.1 | 1 | 1.2 | 1.0 | 4.3 | 0.8 | 2.2 |
| | PROB | .530 | .541 | .106 | .184 | .202 | .338 | .042+ |

| | VAR # | EAR HT ABS | RT LDG ABS | STA GRN ABS | STK LDG ABS | BRT STK ABS | BAR PLT ABS |
|---|---|---|---|---|---|---|---|
| TOTAL | 1 | 41.8 | 98.0 | 6.3 | 99.4 | 92.7 | 99.3 |
| SUM | 2 | 46.5 | 96.0 | 6.9 | 99.1 | 92.7 | 98.6 |
| | LOCS | 8 | 3 | 6 | 3 | 3 | 3 |
| | REPS | 16 | 6 | 12 | 6 | 3 | 6 |
| | DIFF | 4.7 | 2.0 | 0.7 | 0.4 | 0.0 | 0.7 |
| | PROB | .001# | .230 | .427 | .709 | | .730 |

TABLE 2C-continued

PAIRED COMPARISON REPORT
VARIETY #1 = 3730
VARIETY #2 = 3714
* = 10% SIG + = 5% SIG # = 1% SIG

| | VAR # | NLF BLT ABS | FUS ERS ABS | ECB DPE ABS | ECB ILF ABS | ECB 25C ABS | ECB 21T ABS |
|---|---|---|---|---|---|---|---|
| TOTAL | 1 | 5.0 | 8.7 | 95.0 | 4.8 | 4.7 | 3.8 |
| SUM | 2 | 5.3 | 7.7 | 91.7 | 6.8 | 6.9 | 2.3 |
| | LOCS | 3 | 3 | 2 | 4 | 5 | 2 |
| | REPS | 4 | 6 | 6 | 11 | 13 | 6 |
| | DIFF | 0.3 | 1.0 | 3.3 | 2.0 | 2.1 | 1.4 |
| | PROB | .742 | .074* | .500 | .041+ | .022+ | .637 |

TABLE 2D

PAIRED COMPARISON REPORT
VARIETY #1 = 3730
VARIETY#2 = 3563
* = 10% SIG + = 5% SIG # = 1% SIG

| | VAR # | BU ACR ABS | BU ACR % MN | MST ABS | TST WT ABS | SDG VGR ABS | EST CNT ABS | TIL LER ABS | GDU SHD ABS | GDU SLK ABS |
|---|---|---|---|---|---|---|---|---|---|---|
| TOTAL SUM | 1 | 159.6 | 103 | 24.1 | 54.0 | 6.8 | 57.6 | 6.1 | 121.9 | 121.6 |
| | 2 | 153.5 | 98 | 25.6 | 54.5 | 5.3 | 58.4 | 1.0 | 128.3 | 130.1 |
| | LOCS | 133 | 133 | 136 | 105 | 71 | 103 | 2 | 41 | 26 |
| | REPS | 209 | 209 | 214 | 149 | 95 | 145 | 2 | 52 | 34 |
| | DIFF | 6.0 | 5 | 1.5 | 0.5 | 1.5 | 0.8 | 5.1 | 6.4 | 8.4 |
| | PROB | .000# | .000# | .000# | .000# | .000# | .040+ | .212 | .000# | .000# |

| | VAR # | PLT HT ABS | EAR HT ABS | RT LDG ABS | STA GRN ABS | STK LDG ABS | BRT STK ABS | GRN APP ABS | DRP EAR ABS | GLF SPT ABS |
|---|---|---|---|---|---|---|---|---|---|---|
| TOTAL SUM | 1 | 105.2 | 41.7 | 92.2 | 4.6 | 97.1 | 93.2 | 6.2 | 99.9 | 1.0 |
| | 2 | 108.3 | 43.3 | 96.0 | 6.6 | 96.1 | 94.8 | 5.8 | 99.9 | 4.0 |
| | LOCS | 66 | 66 | 61 | 43 | 116 | 34 | 38 | 85 | 1 |
| | REPS | 81 | 81 | 106 | 50 | 170 | 44 | 64 | 127 | 1 |
| | DIFF | 3.0 | 1.6 | 3.8 | 1.9 | 1.0 | 1.6 | 0.4 | 0.0 | 3.0 |
| | PROB | .000# | .001# | .008# | .000# | .158 | .178 | .058* | .494 | |

| | VAR # | NLF BLT ABS | FUS ERS ABS | EYE SPT ABS | COM RST ABS | ECB DPE ABS | ECB 1LF ABS | ECB 25C ABS | ECB 21T ABS |
|---|---|---|---|---|---|---|---|---|---|
| TOTAL SUM | 1 | 5.4 | 8.0 | 4.8 | 6.0 | 99.1 | 5.2 | 5.0 | 3.8 |
| | 2 | 7.3 | 5.0 | 5.2 | 4.5 | 99.6 | 5.1 | 7.0 | 1.9 |
| | LOCS | 6 | 1 | 5 | 2 | 13 | 5 | 12 | 2 |
| | REPS | 8 | 1 | 5 | 2 | 17 | 12 | 22 | 6 |
| | DIFF | 1.8 | 3.0 | 0.4 | 1.5 | 0.5 | 0.2 | 2.0 | 1.9 |
| | PROB | .090* | | .587 | .500 | .342 | .776 | .004# | .425 |

Strip Test Data for Hybrid 3730

Comparison data was collected from strip tests that were grown by farmers. Each hybrid was grown in strips of 4, 6, 8, 12, etc. rows in fields depending on the size of the planter used. The data was collected from strip tests that had the hybrids in the same area and weighed. The moisture percentage was determined and bushels per acre was adjusted to 15.5 percent moisture. The number of comparisons represent the number of locations or replications for the two hybrids that were grown in the same field in close proximity and compared.

Comparison strip testing was done between Pioneer Brand Hybrid 3730 and Pioneer Brand Hybrids 3737,3723, 3733,3714 and 3563. The comparisons come from all the hybrid's adapted growing areas in the United States.

These results are presented in Table 3. Hybrid 3730 has a yield advantage over all of the hybrids. Hybrid 3730 has an income/acre advantage over all but one of the hybrids, 3723, which has a similar income per acre as 3730. The income per acre advantage ranged from $3.46 to $13.80. Hybrid 3730's yield and income advantage plus its advantage for other characteristics over these hybrids will make it an important addition for most of the areas where these hybrids are grown.

Comparison of Key Characteristics for Hybrid 3730

Characteristics of Pioneer Hybrid 3730 are compared to Pioneer Hybrids 3737, 3723, 3733, 3714 and 3563 in Table 4. The values given for most of the traits are on a 1–9 basis. In these cases 9 would be outstanding, while 1 would be poor for the given characteristics. These values are based on performance of a given hybrid relative to other Pioneer commercial, precommercial and competitive hybrids that are grown in research and strip test trials. These performance based values are determined utilizing several factors such as research data, experience the trained corn researchers had in the field, and sales experience with the hybrids in strip tests and the field. These values reflect the hybrid's relative performance to other hybrids for the characteristics listed. Table 4 shows Hybrid 3730 yielded well for its maturity, especially in high population density conditions. Hybrid 3730 has good drydown and early growth when compared to the other hybrids. Hybrid 3730 has overall high yield and other good agronomic characteristics which should make it an important hybrid in its area of adaptation.

TABLE 3

PIONEER HYBRID 3730 VS. PIONEER HYBRIDS 3737, 3723, 3733, 3714 and 3563 FROM 1994 STRIP TESTS

| BRAND | PRODUCT | YIELD | MOIST | INCOME /ACRE | POP K/ACRE | STAND (%) | ROOTS (%) | TEST WT |
|---|---|---|---|---|---|---|---|---|
| PIONEER | 3730 | 164.5 | 22.3 | 330.06 | 25.0 | 95 | 100 | 54.9 |
| PIONEER | 3737 | 158.4 | 20.6 | 323.05 | 24.1 | 94 | 100 | 54.9 |
| Advantage | | 6.1 | −1.7 | 7.01 | 0.9 | 1 | 0 | 0.0 |
| #Comparisons | | 13 | 13 | 13 | 9 | 5 | 3 | 13 |
| Percent Wins | | 76 | 7 | 61 | 66 | 40 | 0 | 38 |
| Prob. of Diff. | | 97 | 99 | 76 | 87 | 16 | 0 | 2 |
| PIONEER | 3730 | 155.5 | 23.4 | 309.06 | 27.3 | 93 | 99 | 56.0 |
| PIONEER | 3723 | 153.8 | 22.2 | 309.43 | 27.7 | 93 | 99 | 56.1 |
| Advantage | | 1.7 | −1.2 | −0.37 | −0.4 | 0 | 0 | −0.1 |
| #Comparisons | | 56 | 56 | 56 | 36 | 27 | 17 | 48 |
| Percent Wins | | 53 | 17 | 51 | 27 | 29 | 5 | 45 |
| Prob. of Diff. | | 79 | 99 | 12 | 73 | 45 | 29 | 10 |
| PIONEER | 3730 | 163.1 | 20.9 | 331.68 | 24.8 | 93 | 95 | 55.8 |
| PIONEER | 3733 | 159.2 | 20.3 | 326.13 | 24.8 | 85 | 96 | 57.9 |
| Advantage | | 3.9 | −0.6 | 5.55 | 0.0 | 8 | −1 | −2.1 |
| #Comparisons | | 307 | 307 | 307 | 193 | 155 | 116 | 291 |
| Percent Wins | | 63 | 30 | 60 | 40 | 56 | 13 | 3 |
| Prob. of Diff. | | 99 | 99 | 99 | 17 | 99 | 15 | 99 |
| PIONEER | 3730 | 171.9 | 17.1 | 362.71 | 28.0 | 87 | 100 | 57.4 |
| PIONEER | 3714 | 165.1 | 16.8 | 348.91 | 27.4 | 90 | 100 | 57.1 |
| Advantage | | 6.8 | −0.3 | 13.80 | 0.6 | −3 | 0 | 0.3 |
| #Comparisons | | 17 | 17 | 17 | 13 | 6 | 4 | 17 |
| Percent Wins | | 70 | 52 | 76 | 46 | 33 | 0 | 52 |
| Prob. of Diff. | | 97 | 79 | 96 | 72 | 45 | 0 | 82 |
| PIONEER | 3730 | 172.2 | 19.6 | 354.67 | 25.4 | 93 | 93 | 56.2 |
| PIONEER | 3563 | 171.7 | 20.5 | 351.21 | 25.5 | 91 | 94 | 56.9 |
| Advantage | | 0.5 | 0.9 | 3.46 | −0.1 | 2 | −1 | −0.7 |
| #Comparisons | | 321 | 321 | 321 | 218 | 159 | 128 | 299 |
| PercentWins | | 53 | 74 | 58 | 44 | 46 | 12 | 14 |
| Prob. of Diff. | | 54 | 99 | 98 | 9 | 98 | 44 | 99 |
| PIONEER | 3730 | 166.8 | 20.5 | 340.95 | 25.4 | 93 | 95 | 56.0 |
| Weighted Avg | | 164.5 | 20.5 | 336.58 | 25.4 | 88 | 95 | 57.2 |
| Advantage | | 2.3 | 0.0 | 4.37 | 0.0 | 5 | 0 | −1.2 |
| #Comparisons | | 714 | 714 | 714 | 469 | 352 | 268 | 668 |
| Percent Wins | | 58 | 49 | 59 | 42 | 49 | 12 | 13 |
| Prob. of Diff. | | 99 | 5 | 99 | 18 | 99 | 36 | 99 |

Note: The probability values are useful in analyzing if there is a real difference in the genetic potential of the products involved. High values are desirable, with 95% considered significant for real differences.

TABLE 4

Hybrid Patent Comparisons-Characteristics
Pioneer Hybrid 3730 vs. Pioneer Hybrids 3737, 3723, 3733, 3714 and 3563

| VARIETY | CRM | SILK CRM | PHY CRM | GDU SILK | GDU PHY | YLD | H/ POP | L/ POP | D/D | S/L | R/L |
|---|---|---|---|---|---|---|---|---|---|---|---|
| 3730 | 99 | 99 | 100 | 1230 | 2390 | 9 | 9 | 7 | 8 | 6 | 6 |
| 3737 | 98 | 98 |  | 1210 |  | 7 | 7 | 7 | 7 | 4 | 5 |
| 3723 | 99 | 101 | 100 | 1260 | 2390 | 7 | 7 | 8 | 6 | 6 | 5 |
| 3733 | 99 | 101 | 101 | 1260 | 2420 | 7 | 6 | 7 | 6 | 4 | 6 |
| 3714 | 100 | 102 |  | 1260 |  | 7 | 7 | 6 | 7 | 5 | 4 |
| 3563 | 103 | 107 | 105 | 1330 | 2530 | 8 | 8 | 7 | 6 | 6 | 6 |

| VARIETY | STA GRN | D/T | TST WT | G/A | E/G | PLT HT | EAR HT | D/E | BRT STK | PRO | P/Y |
|---|---|---|---|---|---|---|---|---|---|---|---|
| 3730 | 6 | 7 | 5 | 6 | 9 | 7 | 5 | 6 | 4 | 5 | 9 |
| 3737 | 4 | 8 | 4 | 4 | 5 | 5 | 4 | 4 | 5 | 5 | 7 |
| 3723 | 6 | 6 | 5 | 5 | 3 | 7 | 8 | 5 | 3 | 6 | 8 |
| 3733 | 7 | 7 | 8 | 7 | 5 | 6 | 6 | 6 | 7 | 5 | 7 |
| 3714 | 5 | 5 | 5 | 5 | 4 | 5 | 7 | 5 | 5 | 5 | 7 |
| 3563 | 6 | 7 | 8 | 6 | 4 | 7 | 4 | 7 | 5 | 4 | 7 |

INDUSTRIAL APPLICABILITY

This invention includes hybrid maize seed of 3730 and the hybrid maize plant produced therefrom. The foregoing was set forth by way of example and is not intended to limit the scope of the invention.

As used herein, the term plant includes plant cells, plant protoplasts, plant cell tissue cultures from which maize plants can be regenerated, plant calli, plant clumps, and plant cells that are intact in plants, or parts of plants, such as embryos, pollen, ovules, flowers, kernels, ears, cobs, leaves, seeds, husks, stalks, roots, root tips, anthers, silk and the like.

Duncan, Williams, Zehr, and Widholm, *Planta*, (1985) 165:322–332 reflects that 97% of the plants cultured which produced callus were capable of plant regeneration. Subsequent experiments with both inbreds and hybrids produced 91% regenerable callus which produced plants. In a further study in 1988, Songstad, Duncan & Widholm in Plant Cell Reports (1988), 7:262–265 reports several media additions which enhance regenerability of callus of two inbred lines. Other published reports also indicated that "hontraditional" tissues are capable of producing somatic embryogenesis and plant regeneration. K. P. Rao, et al., *Maize Genetics Cooperation Newsletter*, 60:64–65 (1986), refers to somatic embryogenesis from glume callus cultures and B. V. Conger, et al., *Plant Cell Reports*, 6:345–347 (1987) indicates somatic embryogenesis from the tissue cultures of maize leaf segments. Thus, it is clear from the literature that the state of the art is such that these methods of obtaining plants are, and were, "conventional" in the sense that they are routinely used and have a very high rate of success.

Tissue culture of maize is described in European Patent Application, publication 160,390, incorporated herein by reference. Maize tissue culture procedures are also described in Green and Rhodes, "Plant Regeneration in Tissue Culture of Maize," *Maize for Biological Research* (Plant Molecular Biology Association, Charlottesville, Va. 1982, at 367–372) and in Duncan, et al., "The Production of Callus Capable of Plant Regeneration from Immature Embryos of Numerous Zea Mays Geneotypes," 165 *Planta* 322–332 (1985). Thus, another aspect of this invention is to provide cells which upon growth and differentiation produce maize plants having the genotype of 3730.

Maize is used as human food, livestock feed, and as raw material in industry. The food uses of maize, in addition to human consumption of maize kernels, include both products of dry- and wet-milling industries.

Maize, including both grain and non-grain portions of the plant, is also used extensively as livestock feed, primarily for beef cattle, dairy cattle, hogs, and poultry.

Industrial uses of maize include production of ethanol, maize starch in the wet-milling industry and maize flour in the dry-milling industry. The industrial applications of maize starch and flour are based on functional properties, such as viscosity, film formation, adhesive properties, and ability to suspend particles. The maize starch and flour have application in the paper and textile industries. Other industrial uses include applications in adhesives, building materials, foundry binders, laundry starches, explosives, oil-well muds, and other mining applications.

Plant parts other than the grain of maize are also used in industry. Stalks and husks are made into paper and wallboard and cobs are used for fuel and to make charcoal.

The seed of the hybrid maize plant and various parts of the hybrid maize plant can be utilized for human food, livestock feed, and as a raw material in industry.

Although the foregoing invention has been described in some detail by way of illustration and example for purposes of clarity and understanding, it will be obvious that certain changes and modifications may be practiced within the scope of the invention, as limited only by the scope of the appended claims.

Applicant has made a deposit of at least 2,500 seeds of Hybird Maize Seed 3730 with the American Type Culture Collection (ATCC), Rockville, Md. 20852 USA, ATCC Deposit No. 209127. The seeds deposited with the ATCC on Jun. 23, 1997, were taken from the deposit maintained by Pioneer Hi-Bred International, Inc., 700 Capital Square, 400 Locust Street, Des Moines, Iowa 50309-2340 since prior to the filing date of this application. This deposit of the Hybird Maize Seed 3730 will be maintained in the ATCC depository, which is a public depository, for a period of 30 years, or 5 years after the most recent request, or for the enforceable life of the patent, whichever is longer, and will be replaced if it becomes nonviable during that period. Additionally, Applicant has satisfied all the requirements of 37 C.F.R. §§1.801–1.809, including providing an indication of the viability of the sample. Applicant imposes no restrictions on the availability of the deposited material from the ATCC; however. Applicant has no authority to waive any restrictions imposed by law on the transfer of biological material or its transportation in commerce. Applicant does not waive any infringement of its rights granted under this patent.

What is claimed is:

1. A hybrid maize plant designated 3730 and its parts, representative seed capable of producing said hybrid maize planting having ATCC accession number 209127.

2. Pollen of the plant of claim 1.

3. An ovule of the plant of claim 1.

4. A tissue of regenerable cells of a hybrid maize plant designated 3730, representative seed said hybrid maize plant having ATCC accession number 209127, wherein the tissue regenerates plants capable of expressing all the morphological and physiological characteristics of hybrid maize plant 3730.

5. A tissue culture according to claim 4, the tissue culture selected from the group consisting of leaves, pollen, embryos, roots, root tips, anthem, silks, flowers, kernels, ears, cobs, husks, stalks, and cells, and protoplasts thereof.

6. A maize plant regenerated from the tissue culture of claim 4, and capable of expressing all the morphological and physiological characteristics of hybird maize plant 3730.

* * * * *

UNITED STATES PATENT AND TRADEMARK OFFICE
CERTIFICATE OF CORRECTION

PATENT NO.    : 5,689,036
DATED         : November 18, 1997
INVENTOR(S)   : Todd Elliott Piper It is certified that error appears in the above-identified patent and that said Letters Patent is hereby corrected as shown below:

<u>Title page,</u>
Item [21], delete "610,905" and insert -- 08/610,905 --.

<u>Column 21,</u>
Line 12, insert -- culture -- between the words "tissue" and "of".

Signed and Sealed this

Twenty-second Day of April, 2003

JAMES E. ROGAN
*Director of the United States Patent and Trademark Office*